US009788804B2

(12) United States Patent
Bailey et al.

(10) Patent No.: US 9,788,804 B2
(45) Date of Patent: Oct. 17, 2017

(54) ANATOMICAL IMAGING SYSTEM WITH IMPROVED DETECTOR BLOCK MODULE

(71) Applicant: Samsung Electronics Co., Ltd., Gyeonggi-do (KR)

(72) Inventors: Eric Bailey, North Hampton, NH (US); Andrew Tybinkowski, Boxford, MA (US)

(73) Assignee: Samsung Electronics Co., Ltd. (KR)

( * ) Notice: Subject to any disclaimer, the term of this patent is extended or adjusted under 35 U.S.C. 154(b) by 114 days.

(21) Appl. No.: 14/805,016

(22) Filed: Jul. 21, 2015

(65) Prior Publication Data

US 2016/0025870 A1    Jan. 28, 2016

Related U.S. Application Data

(60) Provisional application No. 62/027,408, filed on Jul. 22, 2014.

(51) Int. Cl.
| | |
|---|---|
| *A61B 6/03* | (2006.01) |
| *A61B 6/00* | (2006.01) |
| *G01T 1/24* | (2006.01) |
| *G01T 1/29* | (2006.01) |

(52) U.S. Cl.
CPC ............... *A61B 6/032* (2013.01); *A61B 6/03* (2013.01); *A61B 6/035* (2013.01); *A61B 6/4233* (2013.01); *A61B 6/4266* (2013.01); *A61B 6/4405* (2013.01); *G01T 1/243* (2013.01); *G01T 1/2985* (2013.01)

(58) Field of Classification Search
CPC ....... A61B 6/032; A61B 6/035; A61B 6/4233; A61B 6/4266; A61B 6/4405
USPC ................ 378/19, 98.8; 250/370.09
See application file for complete search history.

(56) References Cited

U.S. PATENT DOCUMENTS

| | | | | |
|---|---|---|---|---|
| 5,487,098 A | * | 1/1996 | Dobbs ............. | A61B 6/032 378/19 |
| 5,668,851 A | * | 9/1997 | Dobbs ............. | A61B 6/4291 378/154 |
| 5,802,138 A | * | 9/1998 | Glasser ............ | A61B 6/032 378/19 |
| 5,991,357 A | * | 11/1999 | Marcovici ........ | A61B 6/035 250/370.09 |
| 6,005,908 A | * | 12/1999 | Oppelt ............. | G01T 1/2985 378/11 |
| 6,035,013 A | * | 3/2000 | Orava ............. | G01T 1/2928 250/370.09 |

(Continued)

*Primary Examiner* — Allen C. Ho
(74) *Attorney, Agent, or Firm* — Pandiscio & Pandiscio (57) ABSTRACT

An X-ray detector assembly for an imaging system is provided. The X-ray detector assembly includes a block for mounting to a rotating disc, the block including two opposing end surfaces, two opposing side surfaces and at least one mounting surface, and at least two detector chips, each detector chip including an X-ray detecting surface and an opposing block-facing surface, two opposing end surfaces and two opposing side surfaces, and each detector chip having a flexible bus mounted to the opposing block-facing surface of the detector chip adjacent to a side surface of the detector chip. The at least one mounting surface of the block receives the at least two detector chips in side-by-side disposition, with the buses of the at least two detector chips extending along a side surface of the block.

20 Claims, 11 Drawing Sheets

(56) References Cited

U.S. PATENT DOCUMENTS

| | | | | |
|---|---|---|---|---|
| 6,115,448 A | * | 9/2000 | Hoffman | A61B 6/032 378/19 |
| 6,137,857 A | * | 10/2000 | Hoffman | A61B 6/032 378/19 |
| 6,139,337 A | * | 10/2000 | Englert | A61B 6/035 439/66 |
| 6,144,718 A | * | 11/2000 | Hoffman | G01T 1/2985 378/19 |
| 6,173,031 B1 | * | 1/2001 | Hoffman | A61B 6/5205 250/370.09 |
| 6,259,098 B1 | * | 7/2001 | Vafi | A61B 6/00 250/370.09 |
| 6,292,528 B1 | * | 9/2001 | Wieczorek | A61B 6/032 250/363.02 |
| 6,292,529 B1 | * | 9/2001 | Marcovici | G01N 23/046 250/370.11 |
| 6,362,480 B1 | * | 3/2002 | Peter | G01T 1/2018 250/366 |
| 6,396,898 B1 | * | 5/2002 | Saito | G01N 23/046 378/19 |
| 6,426,991 B1 | * | 7/2002 | Mattson | A61B 6/032 378/19 |
| 6,510,195 B1 | * | 1/2003 | Chappo | G01T 1/2018 250/208.1 |
| 6,522,715 B2 | * | 2/2003 | Hoffman | H01R 12/62 250/370.11 |
| 6,587,538 B2 | * | 7/2003 | Igarashi | A61B 6/06 250/367 |
| 6,621,084 B1 | * | 9/2003 | Wainer | G01T 1/172 250/370.01 |
| 6,671,345 B2 | * | 12/2003 | Vrettos | A61B 6/032 378/19 |
| 6,694,172 B1 | * | 2/2004 | Gagnon | G01T 1/2928 250/363.02 |
| 6,700,948 B2 | * | 3/2004 | Hoffman | A61B 6/032 250/370.09 |
| 6,717,150 B2 | * | 4/2004 | Hoffman | G01T 1/2985 250/367 |
| 6,917,664 B2 | * | 7/2005 | Chappo | A61B 6/032 378/15 |
| 6,925,142 B2 | * | 8/2005 | Pohan | A61B 6/035 250/370.15 |
| 6,982,423 B2 | * | 1/2006 | Elgali | G01T 1/1648 250/370.11 |
| 6,990,176 B2 | * | 1/2006 | Sherman | A61B 6/032 250/370.09 |
| 7,010,088 B2 | * | 3/2006 | Narayanaswamy | G01T 1/249 250/370.09 |
| 7,016,457 B1 | * | 3/2006 | Senzig | A61B 6/032 378/116 |
| 7,029,302 B2 | * | 4/2006 | Sawaya | A61B 6/032 439/260 |
| 7,108,421 B2 | * | 9/2006 | Gregerson | A61B 6/032 378/146 |
| 7,117,588 B2 | * | 10/2006 | Vafi | H01L 27/14658 250/208.1 |
| 7,166,849 B2 | * | 1/2007 | Jiang | G01T 1/2018 250/366 |
| 7,212,604 B2 | * | 5/2007 | Tkaczyk | G01T 1/2985 378/19 |
| 7,235,790 B2 | * | 6/2007 | Hoge | G01T 1/1648 250/370.09 |
| 7,289,336 B2 | * | 10/2007 | Burdick, Jr. | H05K 1/147 257/428 |
| 7,298,814 B2 | * | 11/2007 | Popescu | A61B 6/032 378/19 |
| 7,439,516 B2 | * | 10/2008 | Zeman | G01T 1/249 250/370.11 |
| 7,465,931 B2 | * | 12/2008 | Vogtmeier | A61B 6/4233 250/370.09 |
| 7,525,097 B2 | * | 4/2009 | Dorscheid | G01T 1/2018 250/370.09 |
| 7,560,702 B2 | * | 7/2009 | Meirav | A61B 6/032 250/370.09 |
| 7,564,940 B2 | * | 7/2009 | Mattson | A61B 6/032 250/370.09 |
| 7,570,735 B2 | * | 8/2009 | Konno | A61B 6/585 378/19 |
| 7,606,346 B2 | * | 10/2009 | Tkaczyk | A61B 6/032 250/370.09 |
| 7,792,239 B2 | * | 9/2010 | Nambu | A61B 6/032 378/19 |
| 8,483,362 B2 | * | 7/2013 | Freund | G21K 1/025 378/147 |
| 8,536,552 B2 | * | 9/2013 | Freund | G01T 1/1648 250/370.09 |
| 8,548,119 B2 | * | 10/2013 | Ikhlef | A61B 6/035 378/19 |
| 8,575,558 B2 | * | 11/2013 | Tkaczyk | G01T 1/243 250/370.09 |
| 8,824,635 B2 | * | 9/2014 | Tkaczyk | G01T 1/247 250/363.08 |
| 9,044,151 B2 | * | 6/2015 | Lacey | A61B 6/03 |

\* cited by examiner

(RELATED ART)

Fig. 7

(RELATED ART)

ANATOMICAL IMAGING SYSTEM WITH IMPROVED DETECTOR BLOCK MODULE

REFERENCE TO PENDING PRIOR PATENT APPLICATION

This patent application claims benefit of prior U.S. Provisional Patent Application Ser. No. 62/027,408, filed Jul. 22, 2014 by Neurologica Corp. and Eric Bailey et al. for ANATOMICAL IMAGING SYSTEM WITH IMPROVED DETECTOR BLOCK MODULE, which patent application is hereby incorporated herein by reference.

FIELD OF THE INVENTION

This invention relates to imaging systems in general, and more particularly to anatomical imaging systems.

BACKGROUND OF THE INVENTION

In many situations it can be desirable to image the interior of opaque objects. By way of example but not limitation, in the medical field, it can be desirable to image the interior of a patient's body so as to allow viewing of internal structures without physically penetrating the skin.

Computerized Tomography (CT) has emerged as a key imaging modality in the medical field. CT imaging systems generally operate by directing X-rays into the body from a variety of positions, detecting the X-rays passing through the body, and then processing the detected X-rays so as to build a three-dimensional (3D) data set and a 3D computer model of the patient's anatomy. The 3D data set and 3D computer model can then be visualized so as to provide images (e.g., slice images, 3D computer images, etc.) of the patient's anatomy.

Figure 1:
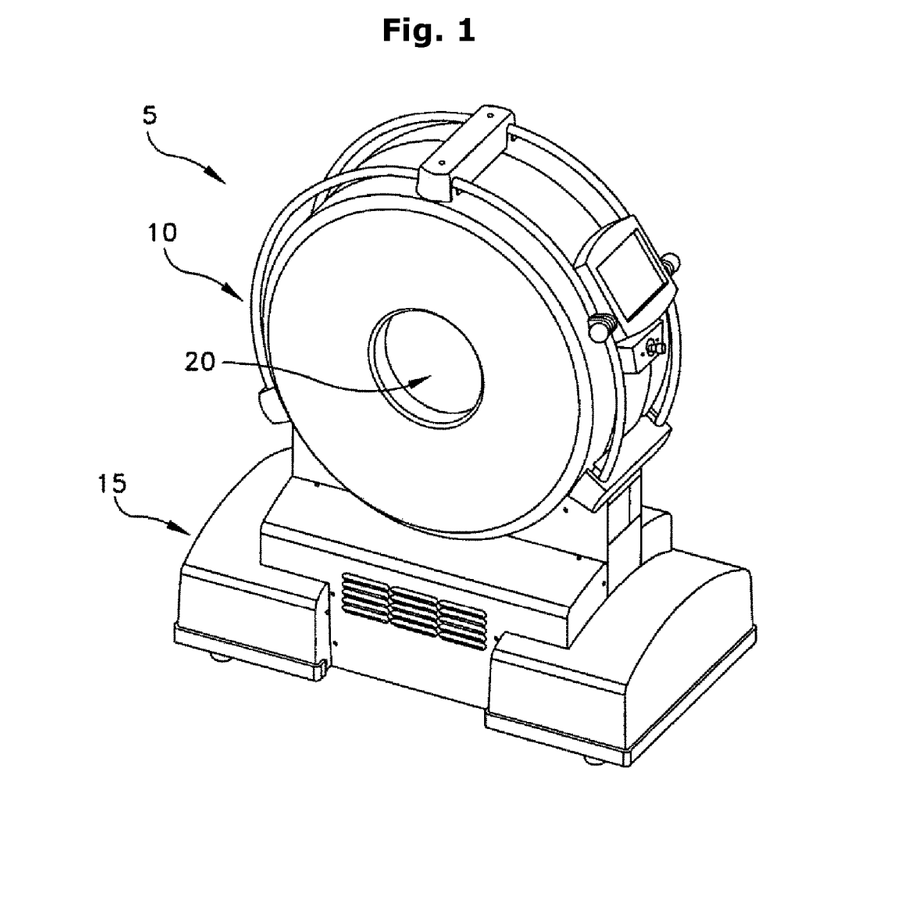
FIGS. 1 and 2 are schematic views showing the exterior of an exemplary CT imaging system.
Figure 2:
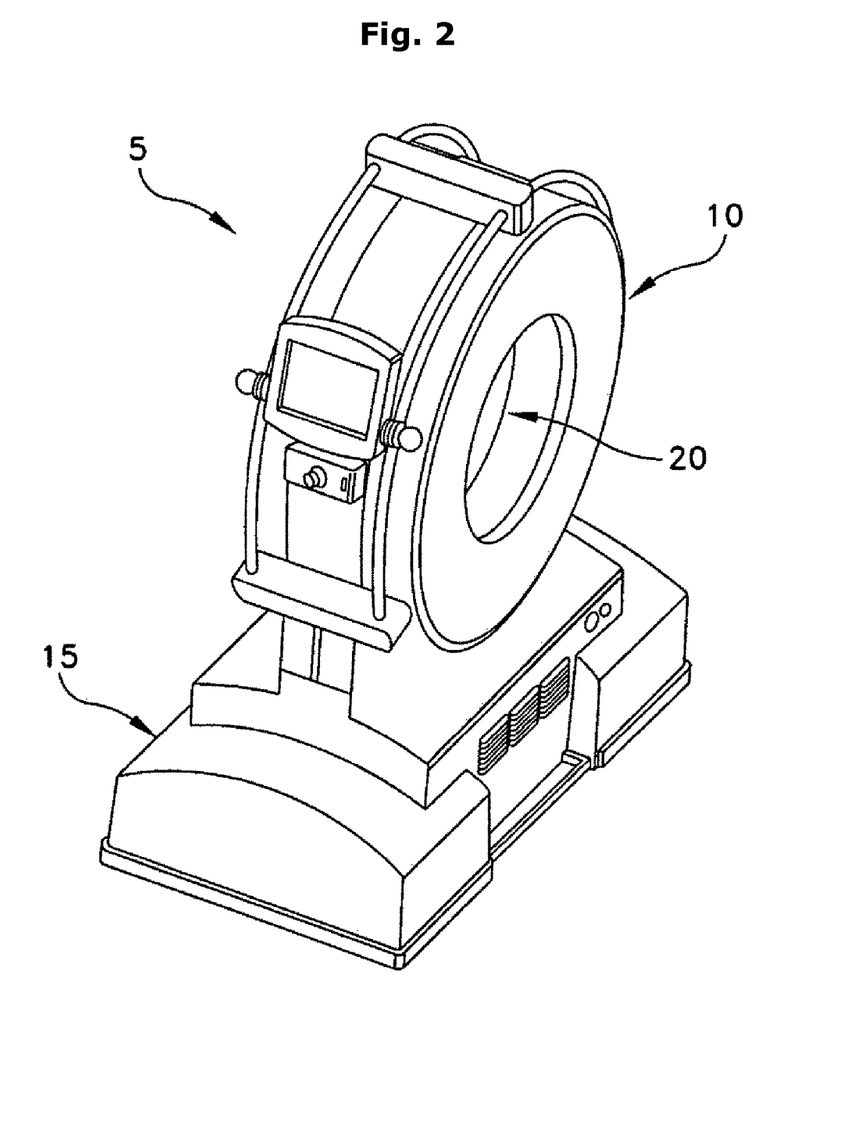

By way of example but not limitation, and looking now at FIGS. 1 and 2, there is shown an exemplary CT imaging system 5. CT imaging system 5 generally comprises a torus 10 which is supported by a base 15. A center opening 20 is formed in torus 10. Center opening 20 receives the patient anatomy which is to be scanned.

Figure 3:
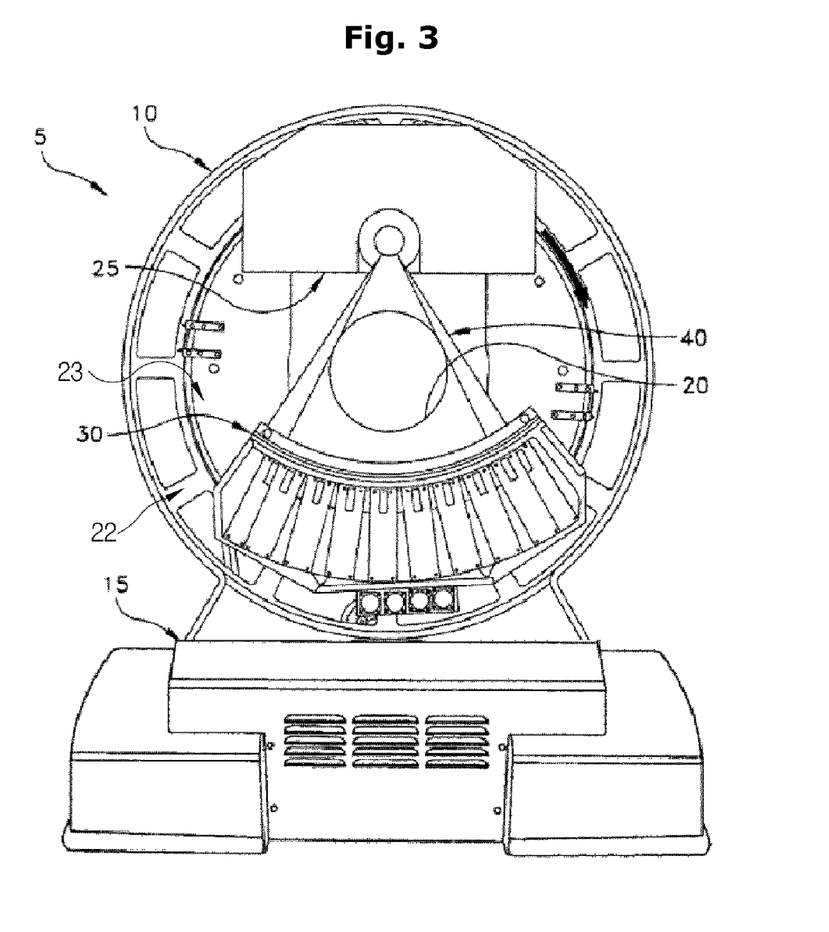
FIG. 3 is a schematic view showing various components in the torus of the exemplary CT imaging system shown in FIGS. 1 and 2.

Looking next at FIG. 3, torus 10 generally comprises a fixed gantry 22, a rotating disc 23, an X-ray tube assembly 25 and an X-ray detector assembly 30. More particularly, fixed gantry 22 is disposed concentrically about center opening 20. Rotating disc 23 is rotatably mounted to fixed gantry 22. X-ray tube assembly 25 and X-ray detector assembly 30 are mounted to rotating disc 23 in diametrically-opposing relation, such that an X-ray beam 40 (generated by X-ray tube assembly 25 and detected by X-ray detector assembly 30) is passed through the patient anatomy disposed in center opening 20. Inasmuch as X-ray tube assembly 25 and X-ray detector assembly 30 are mounted on rotating disc 23 so that they are rotated concentrically about center opening 20, X-ray beam 40 will be passed through the patient's anatomy along a full range of radial positions, so as to enable CT imaging system 5 to create a "slice" image of the anatomy penetrated by the X-ray beam 40. Furthermore, by moving the patient and CT imaging system 5 relative to one another during scanning, a series of slice images can be acquired, and thereafter appropriately processed, so as to create a 3D data set of the scanned anatomy and a 3D computer model of the scanned anatomy. In practice, it is common to configure X-ray detector assembly 30 so that multiple slices of images (e.g., 8 slices, 16 slices, 32 slices, etc.) may be acquired with each rotation of rotating disc 23, whereby to speed up the acquisition of scan data.

In practice, it is now common to effect helical scanning of the patient's anatomy so as to generate a 3D data set of the scanned anatomy, which can then be processed to build a 3D computer model of the scanned anatomy. The 3D data set and 3D computer model can then be visualized so as to provide images (e.g., slice images, 3D computer images, etc.) of the patient's anatomy.

The various electronic hardware and software for controlling the operation of rotating disc 23, X-ray tube assembly 25 and X-ray detector assembly 30, as well as for processing the acquired scan data so as to generate the desired slice images, 3D data set and 3D computer model, may be of the sort well known in the art and may be located in torus 10 and/or base 15.

In many cases CT imaging system 5 is intended to be stationary, in which case base 15 of CT imaging system 5 is set in a fixed position on the floor of a room and a special motorized movable bed is provided to move the patient relative to CT imaging system 5 during scanning. More particularly, with a stationary CT imaging system 5, the patient is brought to the location of CT imaging system 5, the patient is placed on the motorized movable bed, and then the motorized movable bed is used to move the patient relative to CT imaging system 5 (i.e., to advance the patient into center opening 20 of CT imaging system 5) so that some or all of the length of the patient may be scanned by CT imaging system 5.

Figure 4:
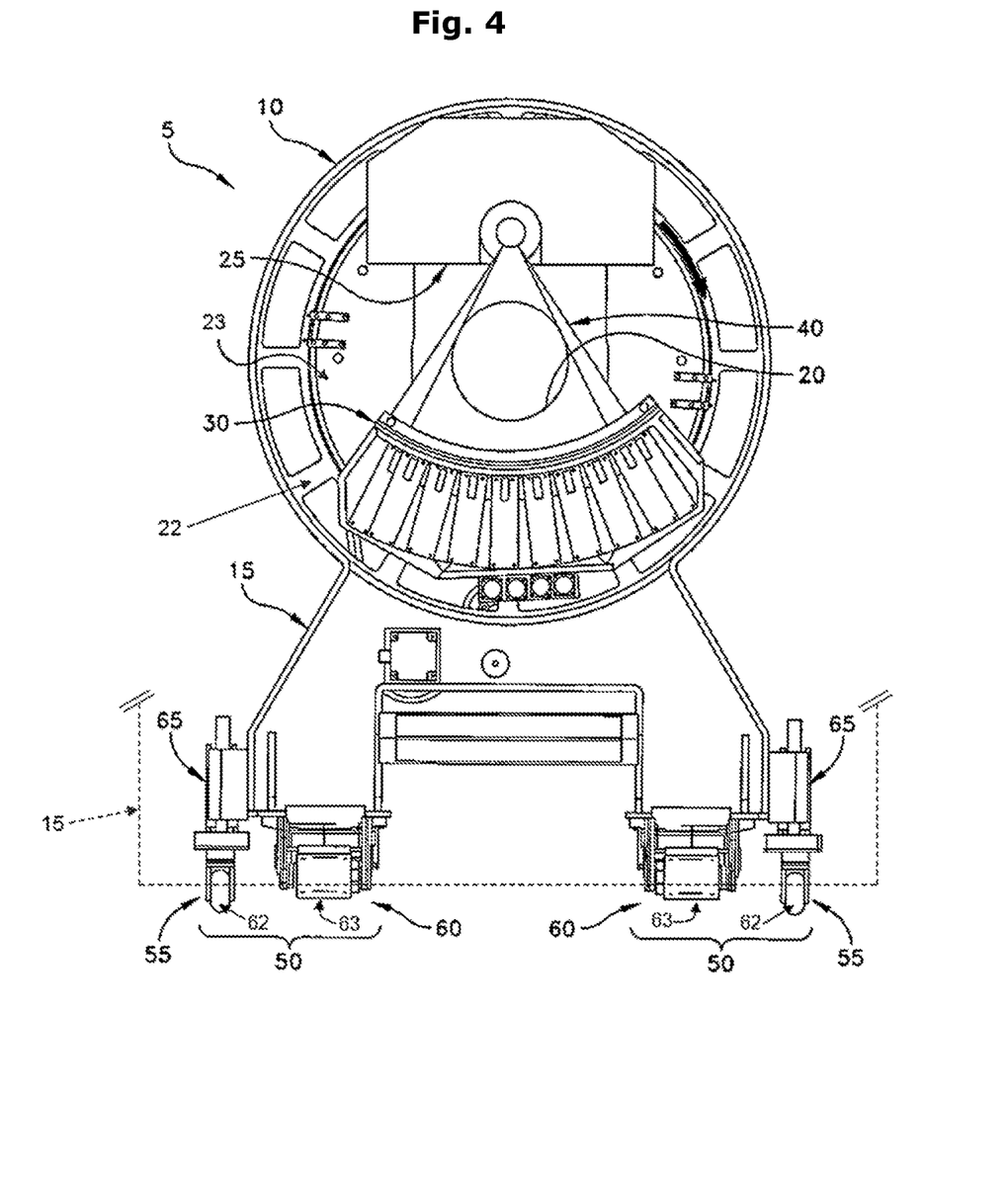
FIGS. 4 and 5 are schematic views showing an exemplary transport assembly for an exemplary CT imaging system.
Figure 5:
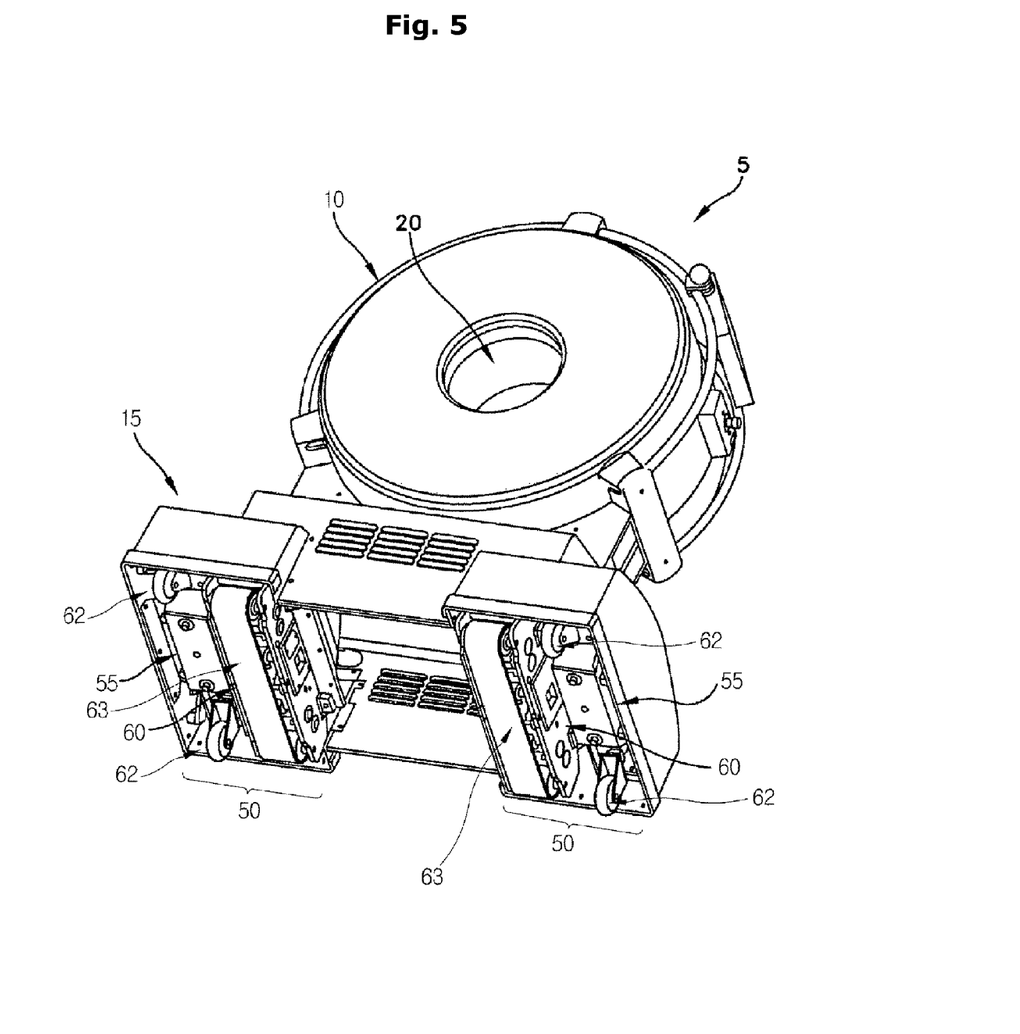

In other cases CT imaging system 5 is intended to be mobile so that the CT imaging system 5 may be brought to the patient and the patient scanned at the patient's current location, rather than requiring that the patient be transported to the location of the CT imaging system 5. Scanning the patient with a mobile CT imaging system 5 can be highly advantageous, since it can reduce delays in patient scanning (e.g., the patient can be scanned in an emergency room rather than waiting to be transported to the radiology department) and/or it can allow the patient to be scanned without requiring movement of the patient (e.g., the patient can be scanned at their bedside in an intensive care unit, "ICU"). To this end, and looking now at FIGS. 4 and 5, base 15 may comprise a transport assembly 50 for (i) moving mobile CT imaging system 5 to the patient prior to scanning and (ii) moving the CT imaging system 5 relative to the patient during scanning. More particularly, transport assembly 50 preferably comprises (i) a gross movement mechanism 55 for moving CT imaging system 5 relatively quickly across room distances, so that the CT imaging system 5 can be quickly and easily brought to the bedside of the patient, such that the patient can be scanned at their bedside without needing to be moved to a radiology department, and (ii) a fine movement mechanism 60 for moving the CT imaging system 5 precisely, relative to the patient, during scanning so that the patient can be scanned on their bed or gurney without needing to be moved onto a special motorized movable bed. In one preferred form of the invention, gross movement mechanism 55 preferably comprises a plurality of free-rolling casters 62, and fine movement mechanism 60 preferably comprises a plurality of centipede belt drives 63 (which can be configured for either stepped or continuous motion, whereby to provide either stepped or continuous scanning of the patient). Hydraulic apparatus 65 permits either gross movement mechanism 55 or fine movement mechanism 60 to be engaged with the floor, whereby to facilitate appropriate movement of mobile CT imaging system 5. Thus, with a mobile CT imaging system 5, the CT mobile imaging system 5 may be pre-positioned in an "out of the way" location (e.g., in an unused corner of an emergency room) and then, when a patient requires scanning, the patient may be quickly and easily scanned at their bedside, by simply moving the mobile CT imaging system 5 to the patient's bedside on gross movement mechanism 55 (e.g., casters 62), and thereafter moving the mobile CT imaging system 5 during scanning on fine movement mechanism 60 (e.g., centipede belt drives 63).

It has been recognized that substantial advantages can be obtained if the time required to scan the patient can be reduced. For one thing, patients sometimes move during the scan, which can result in degraded scan images. A faster scan time means that there is a reduced possibility that the patient will move mid-scan. For another thing, some patient anatomy is normally in motion, e.g., a beating heart. A faster scan time can make it possible to "freeze" the moving anatomy so as to make it possible to image the moving anatomy.

In general, there are two ways to reduce the time required to scan the patient. First, the X-ray detector assembly 30 can be configured to acquire more slice images with each rotation of rotating disc 23, whereby to speed up the acquisition of image data. Thus, over time, so-called "8 slice machines", "16 slice machines", "32 slice machines", etc. have been developed. Second, the speed of rotation of the rotating disc 23 can be increased, whereby to speed up the acquisition of image data.

Unfortunately, increasing the number of slices acquired with each rotation of rotating disc 23, and/or increasing the speed of rotation of the rotating disc 23, can introduce design issues.

Increasing the number of slices acquired by each rotation of rotating disc 23 requires, among other things, additional X-ray detection capacity. Looking now at FIGS. 6 and 7, X-ray detector assembly 30 used in CT imaging system 5 comprises a matrix of detector cells 70 provided in the form of semiconductor detector chips 75. In practice, due to manufacturing considerations, semiconductor detector chips 75 can be made only so large, so it is common to use a plurality of semiconductor detector chips 75, set in side-by-side arrangement, to form an elongated, arcing composite matrix of detector cells to provide the desired X-ray detection capacity.

Figure 6:
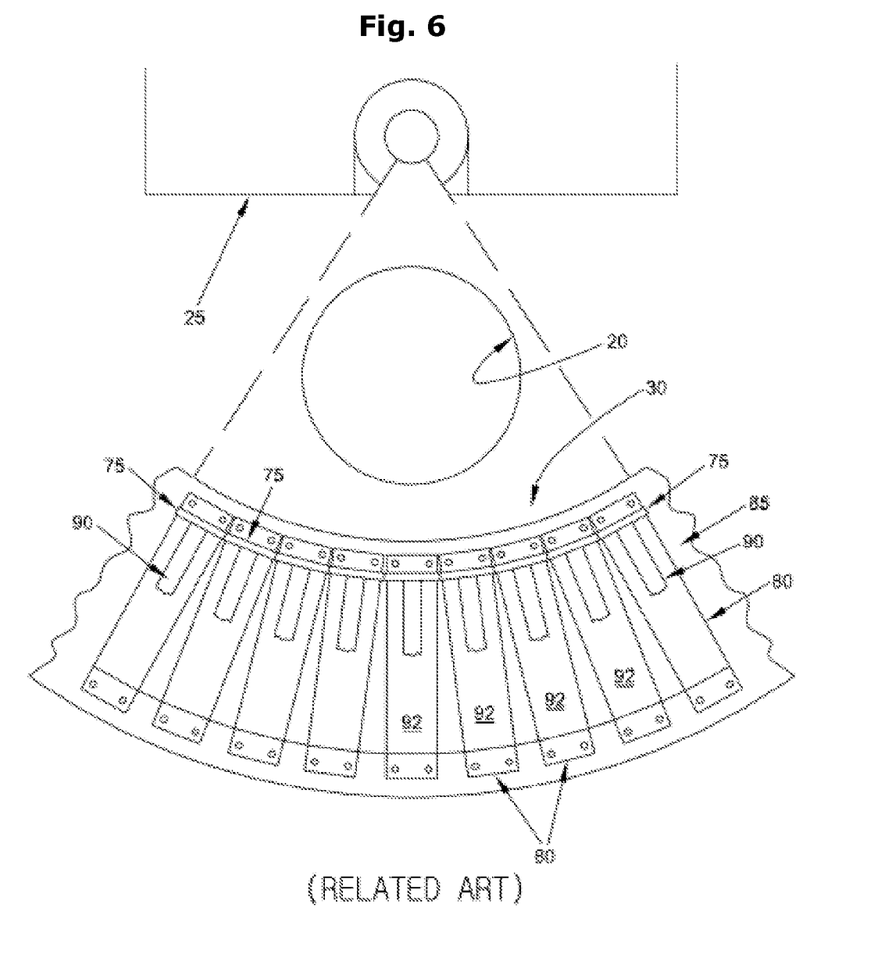
FIG. 6 is a schematic view showing a related art X-ray tube assembly and X-ray detector assembly.
Figure 7:
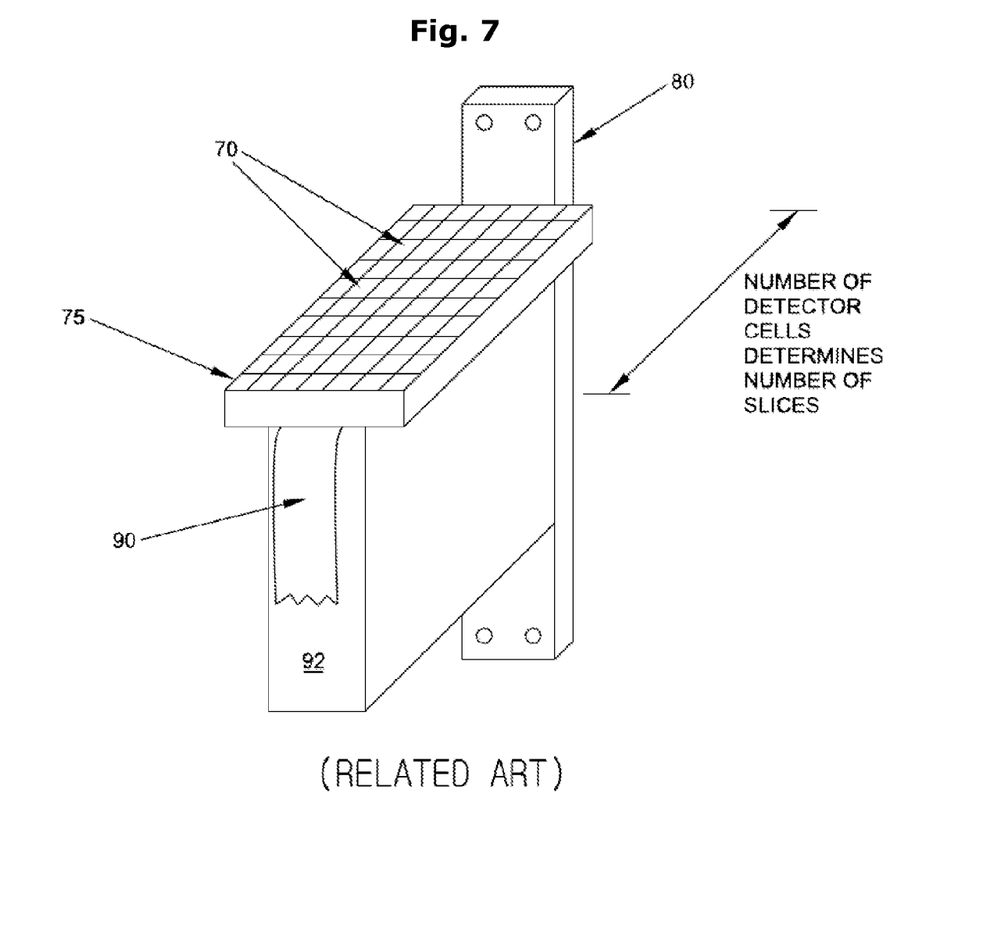
FIG. 7 is a schematic view showing selected components of a related art X-ray detector assembly.

Typically, each semiconductor detector chip 75 is mounted to a block 80, which is in turn mounted to a spine 85, which is in turn mounted to rotating disc 23. Signals received by detector cells 70 on semiconductor detector chips 75 are "taken off" the end of semiconductor detector chips 75 by way of a flexible bus 90, which extends down along the front face 92 of the block 80.

This arrangement has been found to work adequately where X-ray detector assembly 30 is designed to simultaneously collect a moderate number of slices (e.g., 8 slices) with each rotation of rotating disc 23. However, it has been found that this arrangement can be inadequate when using an X-ray detector assembly 30 that is designed to simultaneously collect a large number of slices (e.g., 128 slices).

When it is desirable to collect a larger number of slices (e.g., 128 slices), a larger number of detector cells 70 are required, and a larger bus 90 is also required. It has been found that simply adding additional semiconductor detector chips 75 (and, hence, additional detector cells 70) to block 80 can leave too little space to bring a larger flexible bus 90 off the end of semiconductor detector chip 75 (e.g., extending down along the front face 92 of the block 80 in the manner shown in FIGS. 6 and 7).

In addition to the foregoing, increasing the speed of CT imaging system 5 (e.g., by increasing the speed of rotating disc 23 from 120 rpm to 240 rpm) results in significantly increased forces being exerted on the various components mounted to rotating disc 23 of CT imaging system 5. These significantly increased forces can cause some components (e.g., block 80 and semiconductor detector chips 75) to vibrate and/or otherwise move out of their desired positions (particularly if block 80 were to be axially lengthened to accommodate additional semiconductor detector chips 75), thereby compromising image quality.

Thus there is a need for a CT imaging system having the ability to acquire a greater number of image slices and operate at a higher speed while still acquiring images of acceptable quality.

SUMMARY OF THE INVENTION

These and other objects of the present invention are addressed by the provision and use of an improved imaging system, including a novel X-ray detector assembly which utilizes an improved detector block module.

In one preferred form of the invention, there is provided an X-ray detector assembly for an imaging system, the X-ray detector assembly comprising:

a block for mounting to a rotating disc, the block comprising two opposing end surfaces, two opposing side surfaces and at least one mounting surface; and at least two detector chips, each detector chip comprising an X-ray detecting surface and an opposing block-facing surface, two opposing end surfaces and two opposing side surfaces, and each detector chip having a flexible bus mounted to the opposing block-facing surface of the detector chip adjacent to a side surface of the detector chip;

wherein the at least one mounting surface of the block receives the at least two detector chips in side-by-side disposition, with the buses of the at least two detector chips extending along a side surface of the block.

In another preferred form of the invention, there is provided a method for detecting X-rays, the method comprising:

providing an X-ray detector assembly, the X-ray detector assembly comprising:
  a block for mounting to a rotating disc, the block comprising two opposing end surfaces, two opposing side surfaces and at least one mounting surface; and
  at least two detector chips, each detector chip comprising an X-ray detecting surface and an opposing block-facing surface, two opposing end surfaces and two opposing side surfaces, and each detector chip having a flexible bus mounted to the opposing block-facing surface of the detector chip adjacent to a side surface of the detector chip;
  wherein the at least one mounting surface of the block receives the at least two detector chips in side-by-side disposition, with the buses of the at least two detector chips extending along a side surface of the block; and
detecting X-rays with the X-ray detector assembly.

In another preferred form of the invention, there is provided a CT imaging system comprising:
  a fixed gantry;
  a rotating disc rotatably mounted to the fixed gantry;
  an X-ray tube assembly mounted to the rotating disc; and
  an X-ray detector assembly mounted to the rotating disc,
wherein the X-ray detector assembly comprises:
  a block for mounting to the rotating disc, the block comprising two opposing end surfaces, two opposing side surfaces and at least one mounting surface; and at least two detector chips, each detector chip comprising an X-ray detecting surface and an opposing block-facing surface, two opposing end surfaces and two opposing side surfaces, and each detector chip having a flexible bus mounted to the opposing block-facing surface of the detector chip adjacent to a side surface of the detector chip;

wherein the at least one mounting surface of the block receives the at least two detector chips in side-by-side disposition, with the buses of the at least two detector chips extending along a side surface of the block.

In another preferred form of the invention, there is provided a method for scanning a patient with a CT imaging system, the method comprising:

providing a CT imaging system comprising:
a fixed gantry;
a rotating disc rotatably mounted to the fixed gantry;
an X-ray tube assembly mounted to the rotating disc; and
an X-ray detector assembly mounted to the rotating disc, wherein the X-ray detector assembly comprises:
  a block for mounting to the rotating disc, the block comprising two opposing end surfaces, two opposing side surfaces and at least one mounting surface; and
  at least two detector chips, each detector chip comprising an X-ray detecting surface and an opposing block-facing surface, two opposing end surfaces and two opposing side surfaces, and each detector chip having a flexible bus mounted to the opposing block-facing surface of the detector chip adjacent to a side surface of the detector chip;
  wherein the at least one mounting surface of the block receives the at least two detector chips in side-by-side disposition, with the buses of the at least two detector chips extending along a side surface of the block; and
using the CT imaging system to scan the patient.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

In accordance with the present invention, there is provided an improved CT imaging system 5 that is capable of acquiring a greater number of slice images with each revolution of rotating disc 23 and operating at a higher rotational speed.

Looking now at FIGS. 8-11, there is shown a novel detector block module 105 and other components of an improved CT imaging system 5. Novel detector block module 105 comprises a block 110 and detector chips 115. Block 110 is formed so as to be wide enough to set two detector chips 115 in side-by-side relation, and is robust enough to resist deformation and/or movement during operation of CT imaging system 5 (as is more particularly described below) even when CT imaging system 5 is run at a high rotational speed. Block 110 is preferably formed so as to have two canted surfaces 120 and 125 along its top surface. At least one detector chip 115 is mounted to each of canted surfaces 120 and 125. In one preferred form of the invention, two or more detector chips 115 are mounted serially to each canted surface 120, 125 (see FIGS. 9-11). A flexible bus 130 is mounted to each detector chip 115 as is more particularly described below.

When a detector chip 115 is mounted to a canted surface 120, 125, the detector chip 115 is set at a slight angle to the vertical axis of block 110. See, for example, FIG. 8, which shows the vertical axis C of detector chips 115 set at a slight angle to the vertical axis B of block 110. Significantly, this canted positioning of the detector chip 115 allows the detector cells 70 on that detector chip 115 to be sufficiently aligned with X-ray beam 40 so as to ensure that X-ray beam 40 is properly detected by the detector cells 70 on detector chip 115.

Detector chips 115 are also positioned on block 110 such that a portion of each detector chip 115 sits outboard of a side edge 132 of block 110. See FIGS. 8 and 11. Among other things, such positioning allows the detector chips 115 mounted to a given detector block module 105 to sit directly adjacent to the detector chips 115 mounted to the adjacent detector block modules 105 (see FIG. 11). This feature ensures that there is no gap between detector chips 115 of adjacent detector block modules 105, which could lead to a gap in the image acquired by X-ray detector assembly 30 of CT imaging system 5.

Figure 8:
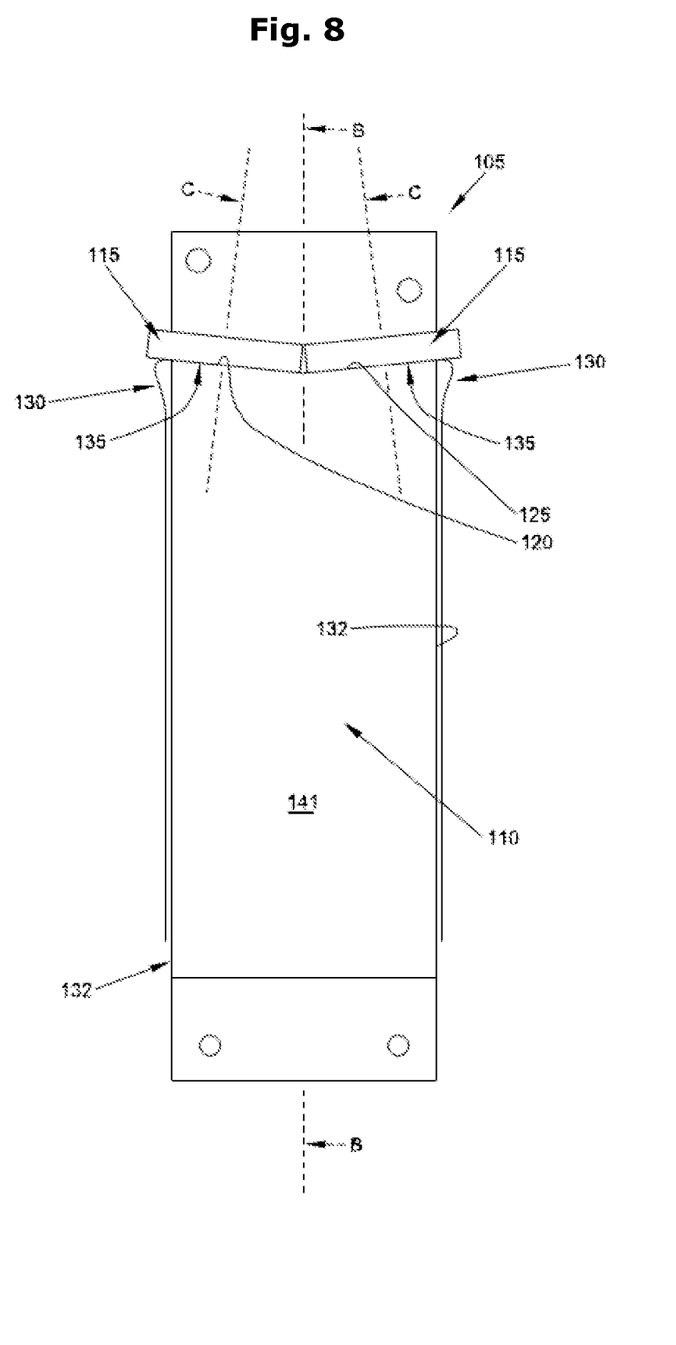
FIG. 8 is a schematic view showing a novel detector block module formed in accordance with the present invention.

A flexible bus 130 is electrically connected to the underside 135 of each detector chip 115 (see FIG. 8). Significantly, flexible bus 130 extends from the underside 135 of each detector chip 115 laterally towards a side edge 132 of block 110 and then downward along that side edge 132 of block 110 in order to connect with associated electrical components carried by a backplane 140 (see FIGS. 8, 9 and 10). Significantly, by having the flexible bus 130 connect to the underside 135 of a detector chip 115 and then extend downward along a side edge 132 of a block 110, a larger flexible bus may be used (since it is not limited by the width of the front face 141 of block 110), and multiple flexible buses 130 may be used (e.g., along both sides 132 of block 110 as seen in FIG. 8, and along the length of each side 132 as seen in FIGS. 9 and 10), so as to accommodate the greater volume of signals being detected by detector chips 115 and transmitted via bus 130.

Further, and significantly, having buses 130 connected to undersides 135 of detector chips 115 and exiting adjacent to the side edges of detector chips 115, and extending buses 130 downward along the side edges 132 of blocks 110, allows each detector chip/bus combination to be manufactured identically. This feature also allows each chip/bus combination to be used at any position (e.g., left, right, front, back, middle) on canted surfaces 120 and 125 of block 110 by rotating detector chip 115 into the appropriate position before mounting. This allows a user to maintain only one kind of detector/bus combination and thereby allows for simpler replacement in the case of a failure of a particular detector chip 115. It also allows a user to maintain a smaller inventory of spare parts.

Figure 9:
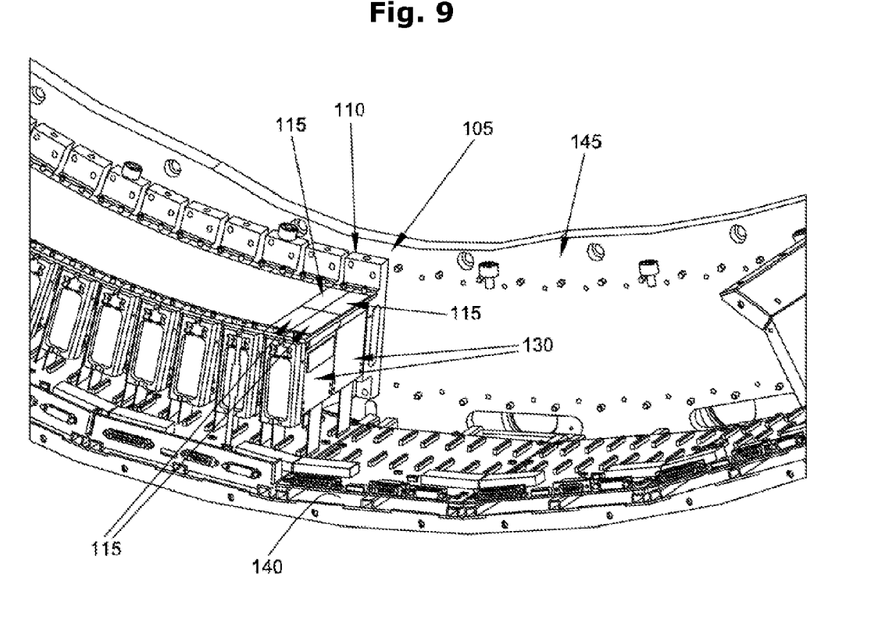
FIGS. 9-11 are schematic views showing a plurality of novel detector block modules formed in accordance with the present invention and shown in relation to other components of a CT imaging system.
Figure 10:
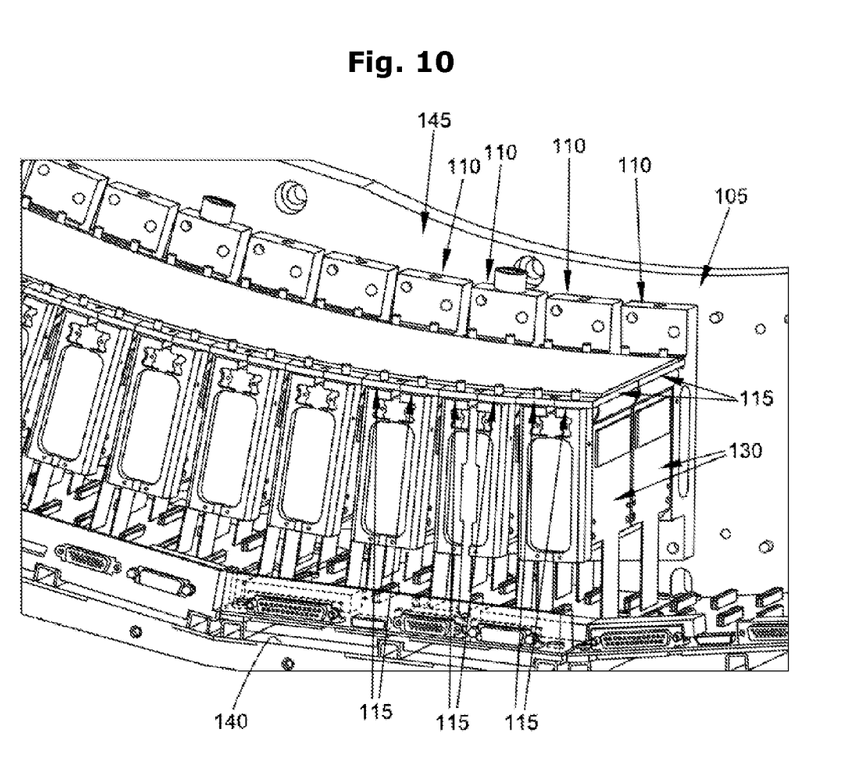
Figure 11:
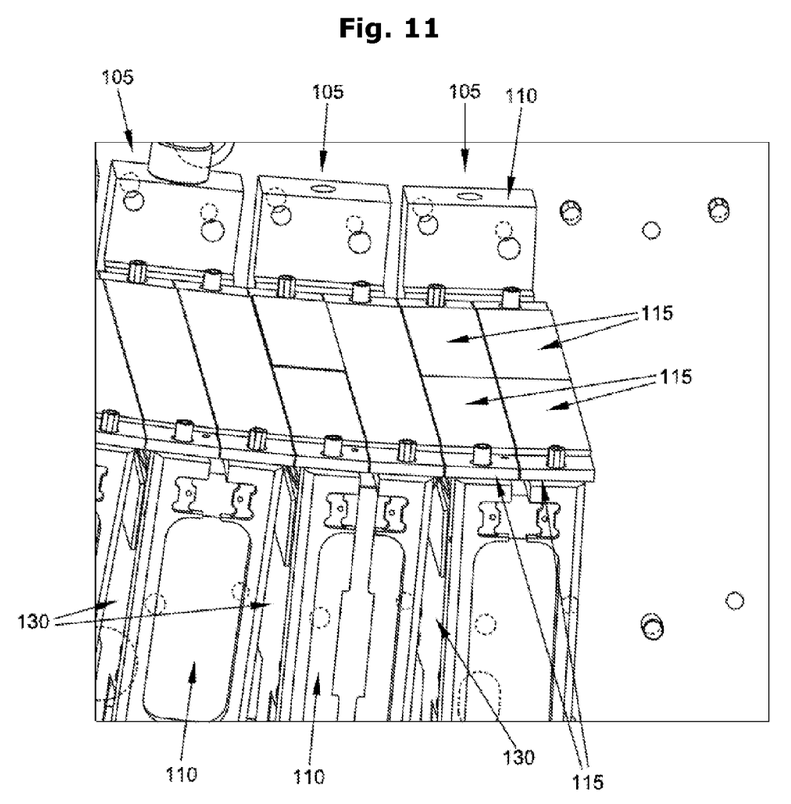

FIGS. 9-11 show the relative position of several detector block modules 105 vis-à-vis one another, and vis-à-vis other components of the improved CT imaging system. Detector block modules 105 are mounted to spine 145. Spine 145 is in turn mounted to rotating disc 23 (not shown in FIGS. 9-11) in a manner which will be apparent to those skilled in the art in view of the present disclosure. Accordingly, during operation of CT imaging system 5, spine 145 rotates along with rotating disc 23, thereby rotating detector block modules 105 as well.

Although FIGS. 9-11 show each detector block module 105 having four detector chips 115 positioned thereon in a 2×2 arrangement, it will be understood that additional detector chips may be placed along the so-called "Z-axis" (i.e., the axis of rotation of rotating disc 23), so as to achieve a 2×3, 2×4, 2×5, 2×6 or other configuration. Furthermore, it will also be appreciated that, if desired, only one detector chip 115 may be positioned on each of the two canted surfaces 120, 125, whereby to produce a 2×1 configuration.

Application to Other Types of Scanning Systems

It should be appreciated that the present invention is not limited to use in medical applications or, indeed, to use with CT machines. Thus, for example, the present invention may be used in connection with CT machines used for non-medical applications, e.g., with CT machines used to scan inanimate objects. Furthermore, the present invention may be used with non-CT-type scanning systems. Thus, for example, the present invention may be used in conjunction with SPECT machines, MRI machines, PET machines, X-ray machines, etc., i.e., wherever the scanning machine may require detectors to be mounted to a rotating disc.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. An X-ray detector assembly for an imaging system, the X-ray detector assembly comprising:
   a block for mounting to a rotating disc, the block comprising two opposing end surfaces, two opposing side surfaces and at least one mounting surface; and
   at least two detector chips, each detector chip comprising an X-ray detecting surface and an opposing block-facing surface, two opposing end surfaces and two opposing side surfaces, and each detector chip having a flexible bus mounted to the opposing block-facing surface of the detector chip adjacent to a side surface of the detector chip;
   wherein the at least one mounting surface of the block receives the at least two detector chips in side-by-side disposition, with the flexible buses of the at least two detector chips extending along a side surface of the block.

2. An X-ray detector assembly according to claim 1, wherein the combined width of the at least two detector chips disposed in side-by-side relation is greater than the width of the at least one mounting surface of the block.

3. An X-ray detector assembly according to claim 1, wherein the at least one mounting surface comprises two canted surfaces.

4. An X-ray detector assembly according to claim 3, wherein the two canted surfaces are canted in opposing directions.

5. An X-ray detector assembly according to claim 1, wherein each of the at least two detector chips is also disposed in an end-to-end configuration with at least one other detector chip.

6. A method for detecting X-rays, the method comprising:
   providing an X-ray detector assembly, the X-ray detector assembly comprising:
      a block for mounting to a rotating disc, the block comprising two opposing end surfaces, two opposing side surfaces and at least one mounting surface; and
      at least two detector chips, each detector chip comprising an X-ray detecting surface and an opposing block-facing surface, two opposing end surfaces and two opposing side surfaces, and each detector chip having a flexible bus mounted to the opposing block-facing surface of the detector chip adjacent to a side surface of the detector chip;
      wherein the at least one mounting surface of the block receives the at least two detector chips in side-by-side disposition, with the flexible buses of the at least two detector chips extending along a side surface of the block; and
   detecting X-rays with the X-ray detector assembly.

7. A method according to claim 6, wherein the combined width of the at least two detector chips disposed in side-by-side relation is greater than the width of the at least one mounting surface of the block.

8. A method according to claim 6, wherein the at least one mounting surface comprises two canted surfaces.

9. A method according to claim 8, wherein the two canted surfaces are canted in opposing directions.

10. A method according to claim 6, wherein each of the at least two detector chips is also disposed in an end-to-end configuration with at least one other detector chip.

11. A CT imaging system comprising:
    a fixed gantry;
    a rotating disc rotatably mounted to the fixed gantry;
    an X-ray tube assembly mounted to the rotating disc; and
    an X-ray detector assembly mounted to the rotating disc, wherein the X-ray detector assembly comprises:
       a block for mounting to the rotating disc, the block comprising two opposing end surfaces, two opposing side surfaces and at least one mounting surface; and
       at least two detector chips, each detector chip comprising an X-ray detecting surface and an opposing block-facing surface, two opposing end surfaces and two opposing side surfaces, and each detector chip having a flexible bus mounted to the opposing block-facing surface of the detector chip adjacent to a side surface of the detector chip;
       wherein the at least one mounting surface of the block receives the at least two detector chips in side-by-side disposition, with the flexible buses of the at least two detector chips extending along a side surface of the block.

12. A CT imaging system according to claim 11, wherein the combined width of the at least two detector chips disposed in side-by-side relation is greater than the width of the at least one mounting surface of the block.

13. A CT imaging system according to claim 11, wherein the at least one mounting surface comprises two canted surfaces.

14. A CT imaging system according to claim 13, wherein the two canted surfaces are canted in opposing directions.

15. A CT imaging system according to claim 11, wherein each of the at least two detector chips is also disposed in an end-to-end configuration with at least one other detector chip.

16. A method for scanning a patient with a CT imaging system, the method comprising:
  providing a CT imaging system comprising:
    a fixed gantry;
    a rotating disc rotatably mounted to the fixed gantry;
    an X-ray tube assembly mounted to the rotating disc; and
    an X-ray detector assembly mounted to the rotating disc, wherein the X-ray detector assembly comprises:
      a block for mounting to the rotating disc, the block comprising two opposing end surfaces, two opposing side surfaces and at least one mounting surface; and
      at least two detector chips, each detector chip comprising an X-ray detecting surface and an opposing block-facing surface, two opposing end surfaces and two opposing side surfaces, and each detector chip having a flexible bus mounted to the opposing block-facing surface of the detector chip adjacent to a side surface of the detector chip;
      wherein the at least one mounting surface of the block receives the at least two detector chips in side-by-side disposition, with the flexible buses of the at least two detector chips extending along a side surface of the block; and
  using the CT imaging system to scan the patient.

17. A method according to claim 16, wherein the combined width of the at least two detector chips disposed in side-by-side relation is greater than the width of the at least one mounting surface of the block.

18. A method according to claim 16, wherein the at least one mounting surface comprises two canted surfaces.

19. A method according to claim 18, wherein the two canted surfaces are canted in opposing directions.

20. A method according to claim 16, wherein each of the at least two detector chips is also disposed in an end-to-end configuration with at least one other detector chip.

* * * * *